April 11, 1972 E. H. SCANLON Plant Pat. 3,107
EUROPEAN BIRD CHERRY TREE
Filed Nov. 28, 1969
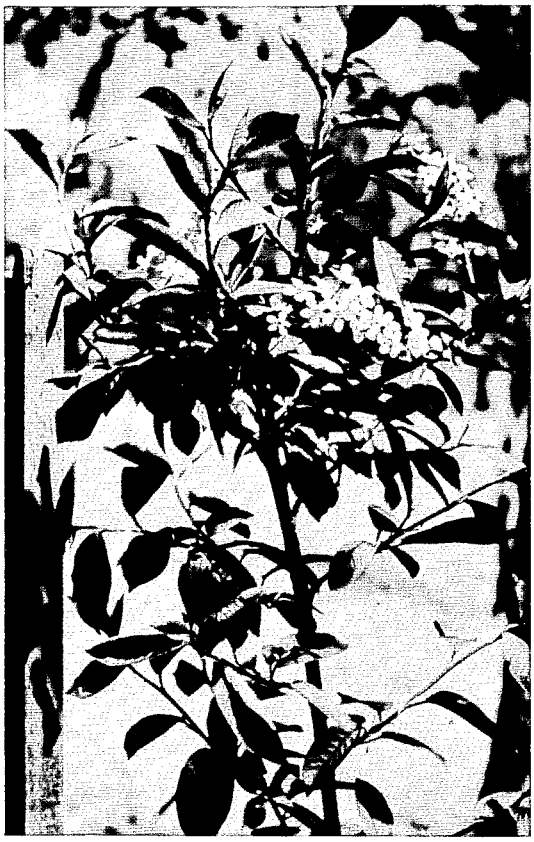

United States Patent Office

Plant Pat. 3,107
Patented Apr. 11, 1972

3,107

EUROPEAN BIRD CHERRY TREE

Edward H. Scanlon, 7621 Lewis Road,
Olmsted Falls, Ohio 44138

Filed Nov. 28, 1969, Ser. No. 880,997
Int. Cl. A01h *5/03*
U.S. Cl. Plt.—37 1 Claim

ABSTRACT OF THE DISCLOSURE

A new and distinct variety of European bird cherry tree (*Prunus padus*) distinguished primarily by a shell pink color of the flower and a somewhat iridescent purplish reddish color of the upper side of the leaf.

The drawing represents a portion of a European bird cherry tree of the new variety showing the flowers and leaves of the distinguishing respective colors.

This variety originated by applicant's discovery in 1964, amongst a bed of European bird cherry seedlings at his grower's nursery in Portland, Oreg., being raised for use as understock in propagating other varieties, of one seedling distinguished from the other in the bed by its iridescent purplish reddish tinged foliage; his then ordering the asexual propagation of that distinctive seedling; the observation in its propagules in the following year of the persistence of the purplish reddish characteristic of the foliage, and in the next year also observation of the distinctive shell pink color of the flowers in both the propagules and parent; and the observation among three hundred individuals in the clone, of the persistence of the distinctive colors of the foliage through four generations and of the flowers through three generations.

The new variety has been asexually reproduced by budding onto European bird cherry understock at Portland, Oreg.

The tree of this new variety is distinguished from trees of the species and other known varieties thereof by the shell pink of the flowers, which are white in the species, and by the marked reddish color of the foliage appearing also somewhat iridescent, in contact with the foliage in the species which is distinctly green and does not, to applicant's knowledge, evidence a reddish color. There is a slight transition of the foliage color, involving some loss of the purplish red, toward a fuller green, which reaches its maximum of transition in August with the foliage never becoming wholly green. The color designations are hereinafter given in terms of the Munsell Nickerson Color Fan. Otherwise the new variety, a deciduous tree, is described as follows:

Branchlets: Glabrous, dark purple with buds of the same color. Branches and small twigs also purplish, ranging from 5RP 8/5 and 5RP 7/9 to 7.5R 5/13 and 7.5R 4/11. Lenticels elongated.

Leaves:

*Shape.*—Elliptic to obovate, acuminate, rounded to subcordate at the base, sharply serrate.

*Size.*—6 to 12 cm. long.

*Petioles.*—1 to 1½ cm. long, usually glabrous, sometimes slightly puberulous, conspicuously glandular.

*Colors.*—A somewhat iridescent markedly purplish reddish color above (ranging from 5R 4/12 to 10R 6/12) tinging the basic green; underside, glaucous with rusty hairs in the axillary veins, and having a solid fall wine color, of about 5R 3/7 to 2.5RP 4/10, with veining 5RP 4/10 to 7.5RP 4/11.

Inflorescence:

*Racemes.*—Flowers occur in a loose drooping racemes having a stalk 10 to 15 cm. long.

*Flowers.*—Shell pink, ranging over 2.5R 9/3 to 2.5R 8/5, 1 to 1½ cm. across, with glabrous pedicels; calyx tube pubescent inside.

I claim:

1. A new and distinct variety of European bird cherry as described and illustrated, distinguished from the species and other known varieties by the pink color of its flowers and the purplish reddish top color of the leaves.

No references cited.

ROBERT E. BAGWILL, Primary Examiner